United States Patent [19]

Kahle, II et al.

[11] Patent Number: 4,927,969
[45] Date of Patent: May 22, 1990

[54] PREPARATION OF ALKYL PRIMARY AMINES

[75] Inventors: Charles F. Kahle, II, Allison Park; Gregory J. McCollum, Gibsonia; Craig A. Wilson, Bakerstown, all of Pa.

[73] Assignee: PPG Industries, Inc., Pittsburgh, Pa.

[21] Appl. No.: 187,786

[22] Filed: May 2, 1988

[51] Int. Cl.$^5$ ............................................. C09C 85/20
[52] U.S. Cl. .................................................. 564/377
[58] Field of Search ........................................ 564/377

[56] References Cited

U.S. PATENT DOCUMENTS 4,111,917 9/1978 Larsen .................................. 528/45
4,547,265 10/1985 Forgione et al. ................ 167/164.6

FOREIGN PATENT DOCUMENTS 0127802 12/1984 European Pat. Off. ............ 564/377

OTHER PUBLICATIONS

Wicks et al., *Jol. of Coating Tech.*, "Reaction of N-(-2-Hydroxyethyl)Amide Compounds", Jul. 1985, pp. 51-61.
*Merck Index*, 8th ed., 1968, pp. 1094, "Urea".
Morrison and Boyd, *Organic Chemistry*, 3rd ed., 1974, p. 686 "Urea".

*Primary Examiner*—Richard L. Raymond
*Assistant Examiner*—Raymond Covington
*Attorney, Agent, or Firm*—Daniel J. Long; Bruce H. Cottrell

[57] ABSTRACT

Alkyl primary amines, e.g., tertiary alkyl primary amines, are prepared by reaction of the corresponding alkyl primary isocyanates with an alkanolamine to form an intermediate area reaction product, followed by heating to decompose the urea reaction product and form the amine product. The amine product can be recovered in high yield by vacuum distillation.

14 Claims, No Drawings

PREPARATION OF ALKYL PRIMARY AMINES

FIELD OF THE INVENTION

This invention relates to the preparation of alkyl primary amines, e.g., tertiary alkyl primary amines such as meta-isopropenyl-alpha,alpha-dimethylbenzyl amine and the like.

BACKGROUND OF THE INVENTION

Methods of preparing tertiary alkyl primary amines, such as meta- or para-isopropenyl-alpha,alpha-dimethylbenzyl amine are disclosed in European Patent Application 127,802. One method describes hydrolyzing the corresponding meta- or para-isomer of isopropenyl-alpha,alpha-dimethylbenzylisocyanate in the presence of a strong acid, such as hydrochloric acid or sulfuric acid, to form isopropenyl-alpha,alpha-dimethylbenzyl amine hydrochloride, followed by reaction of the amine salt with a stoichiometric excess of sodium hydroxide to form the meta- or para-isopropenyl-alpha,alpha-dimethylbenzyl amine. Alternatively, a second method describes heating a solution of meta-isopropenyl-alpha,alpha-dimethylbenzyl isocyanate in methanol to form methyl N-(3-isopropenyl-alpha,alpha-dimethylbenzyl)-carbamate (hereinafter referred to as TMU), mixing the solution containing the TMU with potassium hydroxide (hereinafter referred to as KOH) at a molar ratio of TMU:KOH of from about 0.25 to about 0.5 and in a sufficient amount of 2-methoxyethanol to form a second solution, heating the second solution to convert the TMU to meta-isopropenyl-alpha,alpha-dimethylbenzyl amine, and recovering the amine from the second solution.

A major drawback of the processes in the European Patent Application is the use of strong acids and bases, which can require neutralization and result in greater waste disposal problems.

An alternative method developed to avoid the use of such strong acids and bases is disclosed in co-pending U.S. application Ser. No. 07/187,788, entitled ACRYLIC POLYMERS, by Kania et al., filed on the same date herewith. Such an alternative method involves reaction of an alcohol, such as diacetone alcohol, with a tertiary alkyl primary amine, such as meta-isopropenyl-alpha,alpha-dimethylbenzyl isocyanate, in the presence of a catalyst to form a urethane reaction product, followed by heating for time and at temperatures sufficient to decompose the urethane reaction product and produce the meta-isopropenyl-alpha,alpha-dimethylbenzyl amine. While this method eliminates the use of any strong acids or bases, the yield of this process has been low, generally up to about 50 percent depending upon the choice of alcohol and catalyst.

SUMMARY OF THE INVENTION

The present invention concerns a new, alternative process of preparing alkyl primary amines. The process includes reaction of an alkyl isocyanate with an alkanolamine characterized as containing either primary or secondary amine functionality to form a urea reaction product, and heating the urea reaction product for time and at temperatures sufficient to decompose the urea reaction product and to form a mixture including an alkyl primary amine. In one aspect of the invention, the process involves preparation of a tertiary alkyl primary amine by the reaction of a tertiary alkyl isocyanate with an alkanolamine characterized as containing either primary or secondary amine functionality to form a urea reaction product, and heating the urea reaction product for time and at temperatures sufficient to decompose the urea reaction product and to form a mixture including a tertiary alkyl primary amine. In another aspect of the invention, the process involves preparation of meta-isopropenyl-alpha,alpha-dimethylbenzyl amine by reaction of meta-isopropenyl-alpha,alpha-dimethylbenzyl isocyanate with an alkanolamine to form a urea reaction product, followed by heating to decompose the urea reaction product and form the meta-TMA. The meta-TMA can be readily recovered by vacuum distillation of the urea reaction product.

DETAILED DESCRIPTION

The present process of preparing alkyl primary amines involves the initial reaction of an alkyl isocyanate with an alkanolamine to form a urea reaction product. Subsequent decomposition of the urea reaction product can provide an alkyl primary amine in yields generally exceeding 70 percent. The alkyl primary amine can be, e.g., a primary, secondary or tertiary alkyl primary amine prepared from the corresponding primary, secondary or tertiary alkyl isocyanate.

The alkyl isocyanate starting material can be, e.g., a tertiary alkyl isocyanate of the formula:

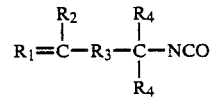

wherein $R_1$ is an alkylidene group having from 1 to 3 carbon atoms; $R_2$ is a hydrogen or an alkyl radical having from 1 to 3 carbon atoms; $R_3$ represents an aromatic hydrocarbon moiety, e.g., a moiety such as phenylene, biphenylene or naphthalene; and $R_4$ is an alkyl radical having from 1 to 3 carbon atoms. Exemplary of such tertiary alkyl isocyanates are meta-isopropenyl-alpha,alpha-dimethylbenzyl isocyanate and para-isopropenyl-alpha,alpha-dimethylbenzyl isocyanate, hereinafter referred to as m-TMI and p-TMI, respectively.

The alkanolamine reacted with the alkyl isocyanate, e.g., the tertiary alkyl isocyanate is characterized as containing either primary or secondary amine functionality. For example, the alkanolamine can be a primary amine such as monoethanolamine, 2-amino-1-propanol, 2-amino-2-methyl-1-propanol, 3-amino-2-propanol, 3-amino-2-methyl-2-propanol and the like or a secondary amine such as diethanolamine and the like. Optionally, the alkanolamine can have greater than two carbons between the amine functionality and the hydroxyl functionality. Preferably, the alkanolamine will have two carbon atoms between the amine functionality and the hydroxyl functionality as this facilitates formation of a stable five-member ring during decomposition of the urea reaction product. The alkanolamine may also be a diglycol amine. Monoethanolamine is the preferred alkanolamine.

The reaction of the alkyl isocyanate and the alkanolamine can generally be conducted in any suitable non-reactive liquid medium such as an organic medium, e.g., lower alcohols, such as ethanol, 1-propanol, 2-propanol, 1-butanol, 2-butanol and the like, methyl isobutyl ketone, N-methylpyrolidone, tetrahydrofuran or the like, an aqueous medium, or mixtures thereof. Alternatively, the reaction may be run neat. Any liquid medium used during the reaction may preferably serve to solubilize the urea reaction product. It may be further desirable that such a liquid medium compatibilize the isocyanate and the alkanolamine reactants.

The alkyl isocyanate and alkanolamine can generally be reacted at a molar ratio of about 1:1 although the alkanolamine is preferably in excess; for example, the alkanolamine to isocyanate ratio may be about 1–2:1 or more.

The reaction of the alkyl isocyanate and the alkanolamine is preferably conducted under nitrogen and in the presence of a free-radical inhibitor, particularly where the alkyl isocyanate includes a polymerizable moiety, e.g., an isopropenyl group such as in meta-TMI or para-TMI. Free-radical inhibitors, e.g., phenolic inhibitors such as 4-methoxyphenol, 4-ethoxyphenol, 2,6-ditertiary-butyl-para-cresol, and the like or quinonic inhibitors such as quinone, 2-methylquinone and the like, can be added in amounts sufficient to prevent free-radical polymerization of any such moieties.

After reaction of the alkyl isocyanate and the alkanolamine to form a urea reaction product, the urea reaction product is heated to decompose the urea and form the alkyl primary amine. Basic or acidic catalysts, such as dibutyltin diacetate, dibutyltin dilaurate, dibutyltin oxide, an alkali hydroxide, such as potassium hydroxide, diazadicyclooctane, dimethylbenzyl amine, dimethylcocoamine and the like, may be added at this stage. In formation of meta-TMA from the urea reaction product of meta-TMI and, e.g., monoethanolamine, it is believed that the equilibrium of the decomposition reaction predominantly favors stability of the urea. As a result, it can be necessary to continuously remove the resultant amine product as it is formed via vacuum distillation.

Vacuum distillation of the urea reaction product can generally be conducted at reduced pressures of from about 0.1 to about 60 torr and at temperatures of from about 50° to 180° Centigrade (C.). The temperatures and pressures can generally be varied although the combination of pressure and temperature must not result in decomposition of the resultant amine product.

In the practice of this invention, it may also be preferred to wash the recovered amine product with water to remove water-soluble impurities. The washing step can be accomplished with deionized water or a dilute, e.g., five percent by weight, solution of sodium chloride in water.

Alkyl primary amines containing a copolymerizable moiety, e.g., an isopropenyl group such as is present in meta-TMA and the like, can be used in acrylic polymerizations to provide primary amine-containing moieties to resultant acrylic polymers as described in the copending U.S. application Ser. No. 07/187,788, entitled ACRYLIC POLYMERS, by Kania et al., filed on the same date herewith.

The following examples are illustrative of the invention:

EXAMPLE 1

A reaction vessel was charged with 173.3 grams (g) of diethanolamine and 158.3 g of methyl isobutyl ketone. Over about 3½ hours, 301.5 g of meta-TMI was slowly added. Infrared analysis showed the absence of any isocyanate. The resultant mixture was admixed with ethyl ether and a dilute aqueous solution of hydrochloric acid. The ethyl ether layer was separated and allowed to dry. After the resultant material was then heated at 120° C. for 24 hours, NMR analysis indicated the presence of meta-TMA.

EXAMPLE 2

A reaction vessel was charged with 91.6 grams (g) of ethanolamine, 200 g of N-butanol, and 0.3 g of the methylether of hydroquinone. Under a nitrogen blanket, dropwise addition of 201.0 g of meta-TMI was conducted over about 1½ hours to control the exotherm of the reaction and maintain the reaction mixture at under about 50° C. Shortly after completion of the TMI addition, infrared analysis indicated that all isocyanate functionality was gone. The mixture was then heated to distill off the N-butanol. Distillation recovered a total of about 152 g. The remaining mixture was vacuum distilled by heating under a vacuum of 20 torr. The mixture was heated to a peak temperature of about 155° C. over about 3½ hours and 181.5 g of the crude product was recovered. Analysis by gas chromatography, NMR, and infrared indicated the product to include predominantly meta-TMA.

Obviously, many modifications and variations of the present invention are possible in light of the above disclosure. It is, therefore, to be understood within the scope of the appended claims, the invention may be practiced otherwise than as specifically described.

What is claimed is:

1. A process of preparing an alkyl primary amine comprising:
   (a) reacting an alkyl isocyanate with an alkanolamine characterized as containing either primary or secondary amine functionality to form a urea reaction product;
   (b) heating the urea reaction product for time and at temperatures sufficient to decompose the urea reaction product and form a mixture including an alkyl primary amine; and
   (c) continuously separating the alkyl primary amine from the reaction mixture formed in step (b).

2. The process of claim 1 wherein in step (c) the alkyl primary amine is separated from the mixture by vacuum distillation of the mixture at a reduced pressure of from about 0.1 to about 60 torr and at temperatures of from about 50° C. to about 180° C.

3. The process of claim 1 wherein the alkyl amine is a tertiary alkyl primary amine and the alkyl isocyanate is a tertiary alkyl isocyanate.

4. The process of claim 3 wherein the tertiary alkyl primary amine is separated from the mixture by vacuum distillation of the mixture at a reduced pressure of from about 0.1 to about 60 torr and at temperatures of from about 50° C. to about 180° C.

5. The process of claim 3 wherein the tertiary alkyl isocyanate is of the formula:

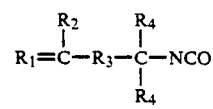

wherein $R_1$ is an alkylidene group having from 1 to 3 carbon atoms; $R_2$ is a hydrogen or an alkyl radical having from 1 to 3 carbon atoms; $R_3$ represents an aromatic hydrocarbon moiety; and $R_4$ is an alkyl radical having from 1 to 3 carbon atoms.

6. The process of claim 5 wherein the tertiary alkyl isocyanate is meta- or para-isopropenyl-alpha,alpha-dimethylbenzyl isocyanate.

7. The process of claim 5 wherein the tertiary alkyl isocyanate is meta-isopropenyl-alpha,alpha-dimethylbenzyl isocyanate.

8. The process of claim 1 wherein the alkanolamine is selected from the group of monoethanolamine or diethanolamine.

9. The process of claim 5 wherein the alkanolamine is selected from the group of monoethanolamine or diethanolamine.

10. The process of claim 6 wherein the alkanolamine is selected from the group of monoethanolamine or diethanolamine.

11. The process of preparing meta-isopropenyl-alpha,alpha-dimethylbenzyl amine comprising:
    (a) reacting meta-isopropenyl-alpha,alpha-dimethylbenzyl isocyanate and an alkanolamine characterized as maintaining either primary or secondary functionality to form a urea reaction product;
    (b) heating a urea reaction product for time and at temperatures sufficient to decompose the urea reaction product and to form a mixture including meta-isopropenyl-alpha,alpha-dimethylbenzyl amine; and
    (c) continuously separating the meta-isopropenyl-alpha,alpha-dimethylbenzyl amine from the mixture formed in step (b).

12. The process of claim 11 wherein the alkanolamine is selected from the group of monoethanolamine of diethanolamine.

13. The process of claim 11 wherein the alkanolamine is monoethanolamine.

14. The process of claim 11 wherein in step (c) the meta-isopropenyl-alpha,alpha-dimethylbenzyl amine is separated from the mixture by vacuum distillation of the mixture at a reduced pressure of from about 0.1 to about 60 torr and at temperatures of from about 50° C. to about 180° C.

* * * * *

UNITED STATES PATENT AND TRADEMARK OFFICE
CERTIFICATE OF CORRECTION

PATENT NO. : 4,927,969

DATED : May 22, 1990

INVENTOR(S) : Charles F. Kahle, Gregory J. McCollum, Craig A. Wilson

It is certified that error appears in the above-identified patent and that said Letters Patent is hereby corrected as shown below:

On the title page, item [57]:

Line 4 of Abstract, "area" should be --urea--.

Signed and Sealed this

Eleventh Day of June, 1991

Attest:

Attesting Officer

HARRY F. MANBECK, JR.

Commissioner of Patents and Trademarks